United States Patent [19]
Pickering et al.

[11] Patent Number: 6,071,865
[45] Date of Patent: *Jun. 6, 2000

[54] NAIL POLISH REMOVER

[76] Inventors: Douglas James Pickering, 10907 W. 99th Pl., Overland Park, Kans. 66214; William Allen Ayres, 7333 Cherokee La., Prairie Village, Kans. 66208

[*] Notice: This patent issued on a continued prosecution application filed under 37 CFR 1.53(d), and is subject to the twenty year patent term provisions of 35 U.S.C. 154(a)(2).

[21] Appl. No.: 08/838,280

[22] Filed: Apr. 16, 1997

[51] Int. Cl.[7] .............................. A61K 7/047; A61K 7/50; C11D 17/00
[52] U.S. Cl. ......................... 510/118; 510/137; 510/403
[58] Field of Search ..................... 510/118, 211, 510/137, 403

[56] References Cited

U.S. PATENT DOCUMENTS

| | | | |
|---|---|---|---|
| 4,085,059 | 4/1978 | Smith et al. | 252/118 |
| 4,530,726 | 7/1985 | Montiel | 134/6 |
| 4,605,670 | 8/1986 | Saito et al. | 514/619 |
| 4,804,486 | 2/1989 | Day | 252/153 |
| 4,824,662 | 4/1989 | Hofmann | 424/61 |
| 4,954,621 | 9/1990 | Masaoka et al. | 536/119 |
| 5,011,621 | 4/1991 | Sullivan | 252/162 |
| 5,024,779 | 6/1991 | Helioff et al. | 252/162 |
| 5,024,780 | 6/1991 | Leys | 252/162 |
| 5,077,038 | 12/1991 | Hofmann | 424/61 |
| 5,098,591 | 3/1992 | Stevens | 252/162 |
| 5,143,639 | 9/1992 | Kawack | 252/162 |
| 5,173,288 | 12/1992 | Everhart et al. | 424/61 |
| 5,310,496 | 5/1994 | Taylor | 252/171 |
| 5,342,536 | 8/1994 | Miner et al. | 252/162 |
| 5,346,640 | 9/1994 | Leys | 252/162 |
| 5,346,652 | 9/1994 | Dotolo et al. | 252/542 |
| 5,372,742 | 12/1994 | Bayless | 252/170 |
| 5,413,795 | 5/1995 | Lee et al. | 424/489 |
| 5,427,710 | 6/1995 | Stevens | 252/166 |
| 5,464,555 | 11/1995 | Bayless | 252/153 |
| 5,468,417 | 11/1995 | LeGrow | 252/174.15 |
| 5,486,305 | 1/1996 | Faryniarz et al. | 252/162 |
| 5,494,611 | 2/1996 | Howe | 252/548 |

FOREIGN PATENT DOCUMENTS

WO 90/03419   4/1990   WIPO.

*Primary Examiner*—Mark Kopec
*Assistant Examiner*—John M. Petruncio
*Attorney, Agent, or Firm*—Kent A. Herink, Esq.; Daniel A. Rosenberg; Davis Brown Law Firm

[57] ABSTRACT

A nail polish removing composition including fatty acid methyl or ethyl esters, N-Methyl-2-pyrrolidone or similar solvent, and a surfactant. The improved nail polish remover has good polish dissolving and removal characteristics, low volatility, low flammability, very low odor, easy clean-up, and skin conditioning properties. In an alternative embodiment, a thickener is added to make the composition a non-pourable gel.

7 Claims, No Drawings

NAIL POLISH REMOVER

BACKGROUND OF THE INVENTION

1. Field of the Invention

The invention relates generally to nail polish removers and, more specifically, to nail polish removers having good polish dissolving and removal characteristics, low volatility, low flammability, very low odor, easy clean-up, and skin conditioning properties.

2. Background of the Prior Art

Finger and toe nail polishes are typically lacquers. Their removal requires a strong solvent to dissolve the dried lacquer. For decades, the nail polish remover or solvent of choice has been acetone, a highly flammable and toxic liquid that in use rapidly evaporates and emits a powerful and offensive odor. Acetone also has a high level of toxicity, facile skin penetration and can leave a white residue on the cleaned nail that can be difficult to remove. Other solvents have included ethyl acetate, and combinations including ethylene and/or propylene carbonate or diethers and diesters. While numerous attempts have been made to develop polish removers that avoid the problems of known removers, there is still a need for improved nail polish removers.

SUMMARY OF THE INVENTION

The invention consists of an improved nail polish remover including a mixture of fatty acid methyl and ethyl esters, a solvent selected from the group including N-Methyl-2-pyrrolidone (NMP), γ-butyrolactone, and dipropylene glycol methyl ether acetate (DPMA), a surfactant, and a thickening agent. The improved formulation does not emit offensive or toxic odors, has a low level of flammability, and a low level of toxicity. The formulation also has a reduced evaporation rate and meets federal and state environmental and hazardous substance laws and regulations.

The improved nail polish remover consists of a mixture, by weight proportion, of between about 5% and about 85% of fatty acid methyl or ethyl esters, between about 15% and about 95% N-Methyl-2-pyrrolidone, γ-butyrolactone, or dipropylene glycol methyl ether acetate, between about 1% and about 10% surfactant, and between about 0% and about 5% thickener. In a preferred embodiment, the improved nail polish remover consists of a mixture, by weight proportion, of between about 40% and about 50% of soybean oil methyl esters, between about 25% and about 50% N-Methyl-2-pyrrolidone, between about 2.5% and about 7.5% surfactant, and between about 0.1% and about 2% thickener.

An object of the invention is to provide a nail polish remover that has improved polish removal characteristics, easy clean-up, and skin conditioning properties.

Another object of the invention is to provide a nail polish remover that has low volatility, low flammability, and very low odor.

A further object of the invention is to provide a nail polish removing composition that is a non-pourable gel.

These and other objects of the invention will be made apparent to one skilled in the art upon a review of this specification and the appended claims.

DETAILED DESCRIPTION OF A PREFERRED EMBODIMENT

It has been found that N-Methyl-2-pyrrolidone combined with compatible fatty acid methyl or ethyl esters and a surfactant provide a nail polish remover with improved characteristics. Other suitable solvents γ-butyrolactone and dipropylene glycol methyl ether acetate (DPMA). The novel, improved remover also may be modified by the addition of a thickener to create a non-pourable gel for ease in application by a user.

The nail polish remover of the present invention is comprised of at least three components, fatty acid methyl or ethyl esters and N-Methyl-2-pyrrolidone (NMP) to dissolve the nail polish and a surfactant to assist in cleaning and dispersing the dissolved polish from the area of the nail. The fatty acid esters have skin conditioning properties that tend to alleviate the drying effect the solvents have on the skin, nail, and cuticle of the user. In a preferred embodiment, a thickener is added to make the composition a non-pourable gel.

N-Methyl-2-pyrrolidone is a dipolar aprotic solvent. It has strong and selective solvency, good stability, low vapor pressure, low toxicity and relatively non-facile skin penetration. It has the following structure:

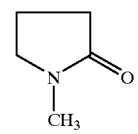

Suitable fatty acid methyl and ethyl esters are those derived from fatty acids and triglycerides of vegetable oils and/or animal fats having carbon-hydrogen chain lengths in the range of between eight and twenty-two carbon atoms, $C_8$–$C_{22}$. In particular, the fatty acid ester profile of soybean oil has been found to be well suited for use in making nail polish removers of the present invention. Surfactants suitable for use in compositions of the present invention include nonionic surfactants, anionic surfactants, amphoteric surfactants and cationic surfactants, including linear alcohols and nonyl phenols compatible with NMP and fatty acid esters. While fatty acid methyl and ethyl esters have surface-acting characteristics, it is contemplated that a separate surfactant will be used in the preferred embodiments of the present invention. Suitable thickeners, if one is to be used, include Baragel® (available from Rheox Incorporated), fumed silica, butyl cellulose and other thickeners, preferably solid form thickeners, compatible with NMP and fatty acid esters.

Nail polish removers of the present invention have low flammability, i.e., a flash point of greater than 199° F., an evaporation rate that is between 200 and 1200 times slower than that of acetone and are only a level 1 (slight) fire hazard. The improved nail polish removers are not hazardous substances under the Comprehensive Environmental Response, Compensation and Liability Act (CERCLA) or the Resource Conservation and Recovery Act (RCRA) and are not subject to the reporting requirements of the Superfund Amendments and Reauthorization Act (SARA), Title III, Sections 311/312 or 313. It also would not be on the Clean Air Act Hazardous Air Pollution list or Subject to California's Proposition 65.

While the solvent used in the preferred embodiment is NMP, other similar solvents may also be used, including specifically solvents γ-butyrolactone and dipropylene glycol methyl ether acetate(DPMA). DPMA is available from ARCO Chemical Company under the tradename ARCO-SOLV®. Gamma—butyrolactone is used as an intermediate with methyl amine to form NMP and has the following structure:

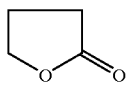

Although the invention has been described with respect to a preferred embodiment thereof, it is to be also understood that it is not to be so limited since changes and modifications can be made therein which are within the full intended scope of this invention as defined by the appended claims.

We claim:

1. A non-pourable gel nail polish removing composition, comprising:
   (a) a skin conditioning and cleaning agent in an amount between about 5 and about 85 percent by weight wherein said skin conditioning and cleaning agent is fatty acid methyl or ethyl esters;
   (b) a solvent in an amount between about 15 and about 95 percent by weight wherein said solvent is N-methyl-2-pyrrolidone;
   (c) a surfactant in an amount between about 1 and about 10 percent by weight; and
   (d) a thickener in an amount not greater than 5 percent by weight to form said non-pourable gel for ease in application by a user.

2. The composition of claim 1, wherein said fatty acid methyl or ethyl esters is present in an amount between about 40 and 50 percent by weight.

3. The composition of claim 1, wherein said N-Methyl-2-pyrrolidone is present in an amount between about 25 and 50 percent by weight.

4. The composition of claim 1, wherein said surfactant is present in an amount between about 2.5 and 7.5 percent by weight.

5. The composition of claim 1, wherein said thickener is present in an amount between about 0.1 and 2 percent by weight.

6. A non-pourable gel nail polish removing composition, comprising:
   (a) a cleaning agent in an amount between about 40 and about 50 percent by weight wherein said skin conditioning and cleaning agent is fatty acid methyl or ethyl esters;
   (b) a solvent in an amount between about 25 and about 50 percent by weight wherein said solvent is N-methyl-2-pyrrolidone;
   (c) a surfactant in an amount between about 2.5 and about 7.5 percent by weight; and
   (d) a thickener in an amount between about 0.1 and 2 percent by weight to form said non-pourable gel for ease in application by a user.

7. A non-pourable gel nail polish removing composition, comprising:
   (a) a skin conditioning and cleaning agent in an amount between about 5 and about 85 percent by weight wherein said skin conditioning and cleaning agent is fatty acid methyl or ethyl esters;
   (b) a solvent in an amount between about 15 and about 95 percent by weight wherein said solvent is selected from the group including N-methyl-2-pyrrolidone, γ-butyrolactone, and dipropylene glycol methyl ether acetate;
   (c) a surfactant in an amount between about 1 and about 10 percent by weight; and
   (d) a thickener in an amount not greater than 5 percent by weight to form said non-pourable gel for ease in application by a user.

* * * * *